(12) United States Patent
AlSaffar

(10) Patent No.: US 9,579,230 B1
(45) Date of Patent: Feb. 28, 2017

(54) METHOD AND ORTHOTIC DEVICE FOR INFANT'S NECK

(71) Applicant: Abdulreidha Abdulrasoul AlSaffar, Sharg (KW)

(72) Inventor: Abdulreidha Abdulrasoul AlSaffar, Sharg (KW)

( * ) Notice: Subject to any disclaimer, the term of this patent is extended or adjusted under 35 U.S.C. 154(b) by 0 days.

(21) Appl. No.: 14/878,102

(22) Filed: Oct. 8, 2015

(51) Int. Cl.
*A61F 5/058* (2006.01)

(52) U.S. Cl.
CPC ............... *A61F 5/05883* (2013.01)

(58) Field of Classification Search
CPC .. A61F 5/05883; A61F 5/055; A61F 5/05816; A61F 5/05833; A61F 5/05; A61F 5/058; A61F 5/05808; A61F 13/12; A61F 13/128; A61F 5/04; A61F 5/042; A61F 5/048
USPC ..................... 602/18; 119/712, 815
See application file for complete search history.

(56) References Cited

U.S. PATENT DOCUMENTS

| | | |
|---|---|---|
| 3,049,120 A | 8/1962 | Marcus |
| 4,088,129 A | 5/1978 | DiGiulio |
| 4,180,870 A | 1/1980 | Radulovic et al. |
| 4,244,359 A | 1/1981 | Dieterich |
| 4,320,747 A | 3/1982 | Daniell, Jr. |
| 4,608,970 A | 9/1986 | Marck et al. |
| 4,649,906 A | 3/1987 | Spademan |
| 5,002,044 A | 3/1991 | Carter |
| 5,183,036 A | 2/1993 | Spademan |
| 5,308,312 A | 5/1994 | Pomatto et al. |
| 5,385,536 A | 1/1995 | Burkhead et al. |
| 5,421,810 A | 6/1995 | Davis et al. |
| 5,503,621 A | 4/1996 | Miller |
| 5,538,499 A | 7/1996 | Schwenn et al. |
| 5,632,722 A * | 5/1997 | Tweardy ............... A61F 5/055 128/DIG. 23 |
| 6,533,741 B1 | 3/2003 | Lee et al. |
| 7,083,583 B2 | 8/2006 | Opahle et al. |
| 7,608,052 B1 * | 10/2009 | Baker ................... A61F 5/055 128/DIG. 23 |
| 7,841,998 B2 | 11/2010 | Pomeroy et al. |
| 7,988,652 B2 | 8/2011 | Chao |
| 8,251,934 B2 | 8/2012 | Bonutti |
| 8,998,833 B1 | 4/2015 | Alsaffar |

(Continued)

FOREIGN PATENT DOCUMENTS

WO     WO 03079941 A1 * 10/2003 ............. A61F 5/055

*Primary Examiner* — Victoria J Hicks
*Assistant Examiner* — Michelle J Lee
(74) *Attorney, Agent, or Firm* — Hauptman Ham, LLP

(57) ABSTRACT

An orthotic device for correcting an abnormality in a newborn baby's neck includes a three element rigid or semi-rigid support member. The support member includes three elements, each in the shape of a frustum of a cone with one element stacked on top of another. The first or bottom element has a larger open base and a smaller upper portion and flares outwardly from top to bottom from vertical by about 20°. The middle element flares outwardly from bottom to top by about 20° and is superimposed on the first element. However, the second element is rotatably fixed to the first element and is rotatable in about one mm increments. The upper element flares outwardly from vertical by about 45°. A method for correcting an abnormality in a newborn's neck in one mm increments per day using the aforementioned device is also disclosed.

6 Claims, 3 Drawing Sheets

(56) References Cited

U.S. PATENT DOCUMENTS

2012/0330204 A1  12/2012  Baldauf et al.

* cited by examiner

METHOD AND ORTHOTIC DEVICE FOR INFANT'S NECK

FIELD OF THE INVENTION

This invention relates to orthopedic methods and devices for newborn babies and more particularly to orthotic methods and devices for correcting skeletal abnormalities in a newborn baby's neck.

BACKGROUND FOR THE INVENTION

Some babies are born with skeletal abnormalities as for example in the hands, feet, shoulders, arms, legs, fingers, thumb, neck and knees. My co-pending U.S. patent application Ser. No. 14/752,959 and Ser. No. 14/178,676, respectively are entitled "Orthotic Method and Device for Newborn Babies" and relates more specifically to orthopedic devices and methods for correcting abnormalities in the feet and toes of newborn human babies. The second of my previously filed U.S. patent applications is entitled "Orthopedic Device and Method for Correcting Skeletal Abnormalities in a New-Born Baby" relating more specifically to method and devices for correcting abnormalities in the wrist, hands, fingers and thumbs of a newborn baby.

A U.S. Patent of Pomatto et al. U.S. Pat. No. 5,308,312 discloses a cranial remodeling orthosis. As disclosed therein a cranial remodeling orthosis is shaped to extend across the top of the head with the pending regions closely confining the temporal bone regions and the mastoid process regions of the cranium. The orthosis is self-suspending and preferably includes an elastic band for imparting ear-to-ear rigidity to the device.

A more recent U.S. Patent Publication No. 2012/0330204 discloses therapeutic cushioning and devices for assisting respiration of and administering fluid to a patient. As disclosed therein, the invention is directed to both therapeutic cushioning designed to support the head of a patient in bed to improve respiration and a series of devices designed to assist a patient's respiration and administer fluid to the patient, by ensuring such devices cannot be inadvertently removed from the patient in the absence of medical personnel and cause unwanted injury to the patient. At the same time, a device is provided to assist a patient's breathing in the absence of such assistive device, e.g. during sleep.

Finally, a U.S. Patent of Bonutti U.S. Pat. No. 8,251,934 discloses an orthosis and method for cervical mobilization. The patent discloses a method of using a neck brace to move a neck of a person or stabilize the neck includes connecting a vest of the neck brace to a torso of a person. A support member of the neck brace is connected to the vest. A chin support of the neck brace is connected to a chin of the person. Force is applied between the support member and the chin support to move the chin support relatively to the support member. A cam member of the neck brace guides movement of the chin support relative to the support member.

Notwithstanding the above, it is presently believed that there is a need and a potential commercial market for an improved device for correcting skeletal abnormalities in a newborn human baby. There should be a potential commercial market because there are babies that need to overcome abnormalities in a newborn baby's neck. Further, such methods and devices can be used to correct such abnormalities within hours of the patient's birth and that will make considerably improvements within days at a relatively modest cost.

SUMMARY OF THE INVENTION

An orthotic method and device for correcting a skeletal abnormality in a newborn baby's neck includes the use of a three element, rigid or semi rigid shell like support that partially encircles a newborn patient's neck and supporting and positioning a patient's head with respect to a patient's torso. The three level or three element support includes a first or lower element that defines an inverted frustum of a cone extending around and abutting both of the sides and the back of a patient's lower portion of the patient's neck but remains open along the front of the patient's neck. A larger open end of the inverted cone engages the top of the patient's shoulders. Further, clamping means are provided for fastening an upper portion of the first level or element against the patient's neck without obstructing the patient's esophagus and/or airway. A second level or element of the support also defines a frustum of a cone opened along the front of a patient's neck with its open smaller lower end engaging the opened smaller upper end of the first element and rotationally attached thereto. A second clamping means for fastening the second element around the patient's neck is provided and does not obstruct the patient's esophagus or windpipe. An important element in the present invention resides in an adjustment mechanism for adjusting the rotational movement between the first element of the device and the second element on the second level of the device in one millimeter increments. Finally, a third element or third level of the device defines a frustum of a cone partially encircling a patient's neck with a smaller end of the frustum of the cone engaging and fixed to an upper larger opening of the second element but flared outwardly at a greater angle than the second level for supporting a lower portion of the patient's head.

In addition, a second embodiment of the invention relates to a method for correcting skeletal abnormality in a newborn baby's neck that comprises the following steps. Providing a three element with each element on a separate level shell like support as described above. Following that the second step calls for adjusting the shell like support to fit the baby's neck and lower part of the baby's head and the next step making adjustments to increase the bias by an increment of about one millimeter and continue such bias for a 24-hour period. In the final steps, the adjustment step is repeated once each day until the abnormality has been moved to a normal position and stabilized.

The invention will now be described in connection with the following figures wherein like numerals have been used to indicate like parts.

DESCRIPTION OF THE PREFERRED EMBODIMENTS OF THE INVENTION

In the practice of the present invention, it is highly desirable to initiate treatment of a newborn baby as soon as possible and if possible within hours of the birth of an infant. For example, it is preferred to fit an orthotic device to a newborn baby's neck within four to six hours of birth and if at all possible within ten to twelve hours of birth.

In practice, an obstetrician with a modicum of experience in the delivery of human babies will recognize a need for correcting a skeletal abnormality of the neck in an initial examination of the baby.

Figure 1:
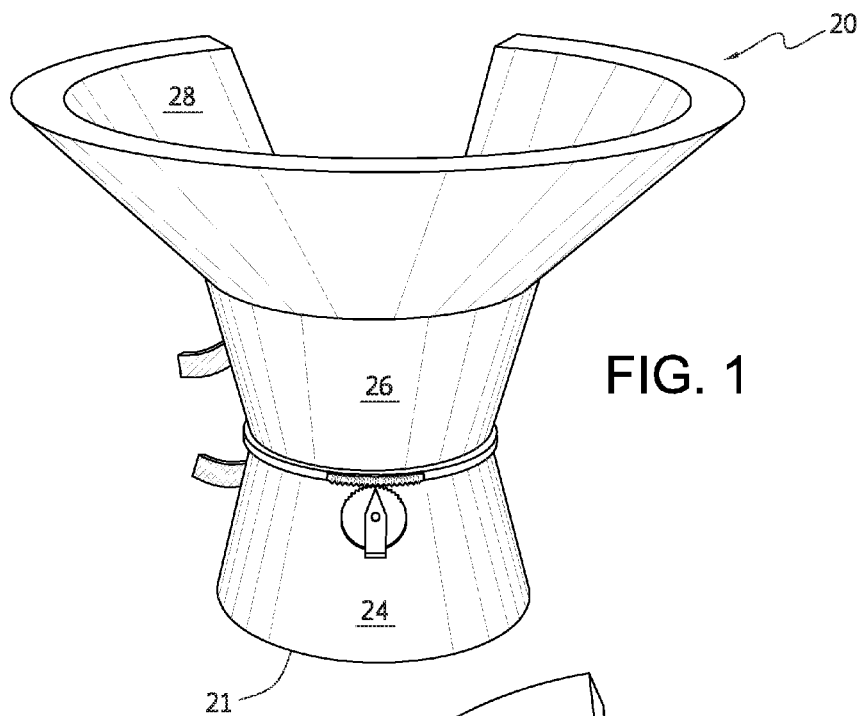
FIG. 1 is a schematic perspective illustration of a device for correcting abnormalities in a newborn baby's neck.
Figure 2:
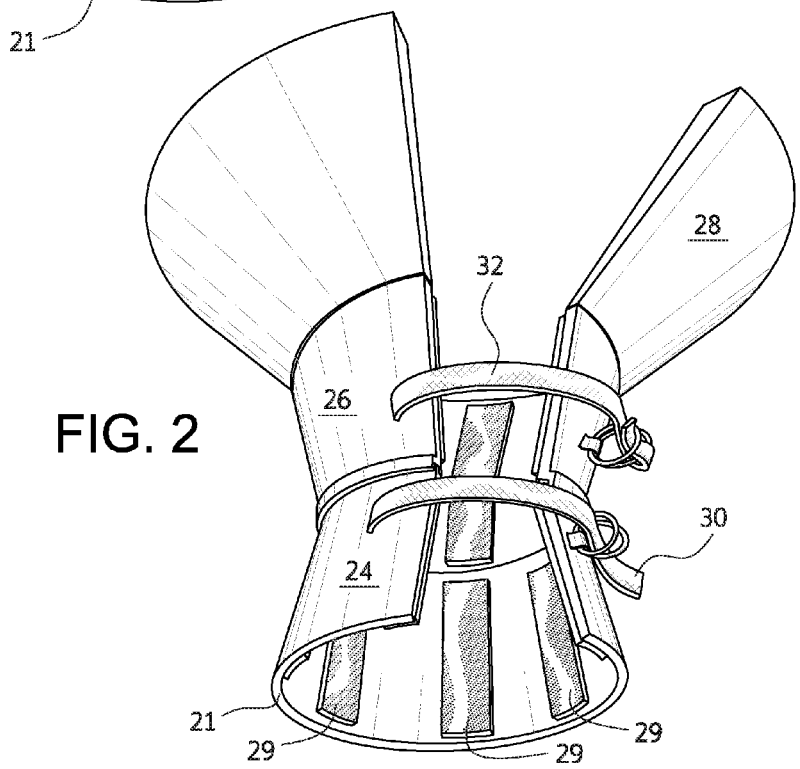
FIG. 2 is a schematic perspective view of the device shown in FIG. 1 but taken from the opposite side of the device.
Figure 3:
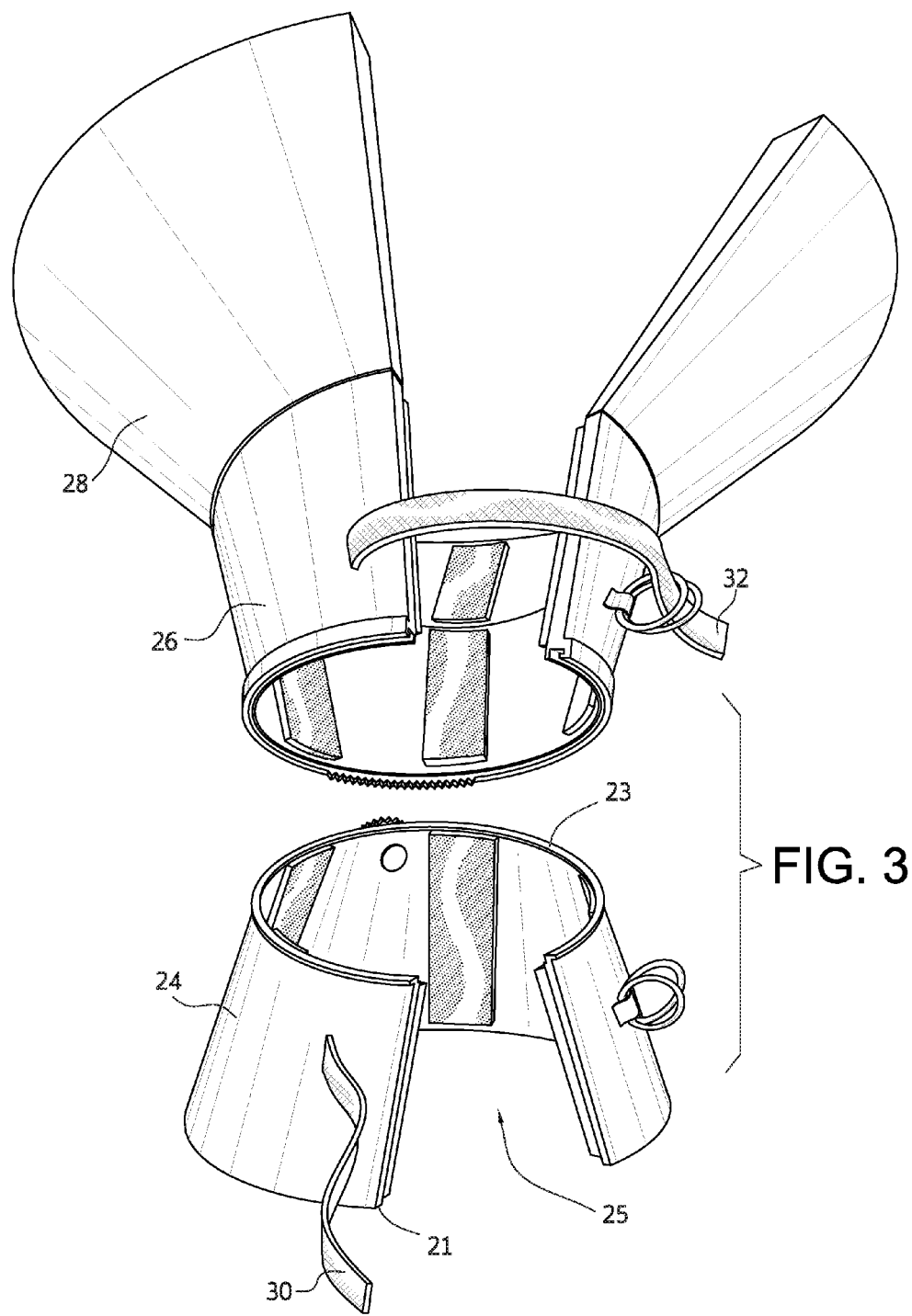
FIG. 3 is an exploded perspective view of FIG. 2 that shows the mechanism between the bottom and middle elements of the support for rotating the middle section with respect to the bottom section in one millimeter increments.

Referring now to FIGS. 1-3, an orthotic device 20 for correcting a skeletal abnormality in a newborn baby's neck in accordance with a preferred embodiment of the invention is illustrated. The orthotic device 20 will be manufactured in extremely small sizes to accommodate very small even premature babies to those with weights of eight to ten pounds or more.

As illustrated more clearly in FIGS. 1 and 2, the orthotic device 20 for correcting a skeletal abnormality in the neck of a newborn baby includes a support member 22 of a rigid or semi rigid material as for example polyethylene (PE), polyvinylchloride (PVC) or polyethylene terephthalate (PET), polypropylene and the like. The support 22 is of extremely lightweight and includes three parts or elements, a lower element 24, a middle element 26 and an upper element 28. The elements are connected together on top of one another.

As illustrated, the elements are shown in a vertical arrangement for convenience even though a newborn baby will normally be lying down on a generally horizontal plane.

As illustrated, a first or lower element 24 is shaped like an inverted frustum of a cone with a slightly larger opened base 21 that abuts against the newborn baby's shoulders. The element 24 also has an upper smaller opened end 23 and defines an opened portion 25 that extends from the top to the bottom of the element 24. The open portion 25 is aligned with the front of the newborn's neck so that the baby's esophagus and windpipe are not obstructed.

Referring now to FIG. 2, the open portion 25 of element 24 is held together by a clamp 30 to retain an open area that extends across the outer surfaces of the element 24 in an upper portion thereof. As illustrated, a portion of the clamp 30 extends around and is fixed to an inner surface along the sides and back of the element 24 and is fixed thereto. Any suitable construction for the clamp can be used but preferably one that has a mechanism for adjustment and extends from one outer surface to the opposite outer surface of the element 24.

The middle element 26 includes a smaller opening in a bottom portion thereof with a diameter that is essentially the same as the diameter of the smaller open end 23 of the element 24. The middle element 26 also includes a clamp 32. The clamp 32 is essentially parallel to the clamp 30 and extends across the outer surfaces of the middle element 26 to maintain the open portion 25 in a position that does not obstruct the esophagus or windpipe of the patient.

The upper element 28 also defines the shape of a frustum of a cone with an extension of the open portion 25 extending from a lower portion to the top thereof. The upper portion 28 flares outwardly from the bottom to the top at a considerably greater angle than the flare in the middle portion 26 and lower portion 24. For example, the upper portion 28 extends outwardly from a vertical axis at an angle of 40° to 50° and preferably about 45°.

By contrast, the middle portion flares outwardly from the bottom to the top from about 15° to 25° from vertical and preferably by about 20° from the bottom to its top. Finally, the bottom element 24 flares outwardly from its top to its lower portion by about 15° to about 25° and preferably about 20°.

As illustrated in FIG. 2, the orthotic device 20 includes soft padding 29 on the upper surface of the third or upper element 28 to position and cradle a newborn's head.

A method in accordance with a preferred embodiment of the invention will now be described in connection with FIG. 4.

Figure 4:
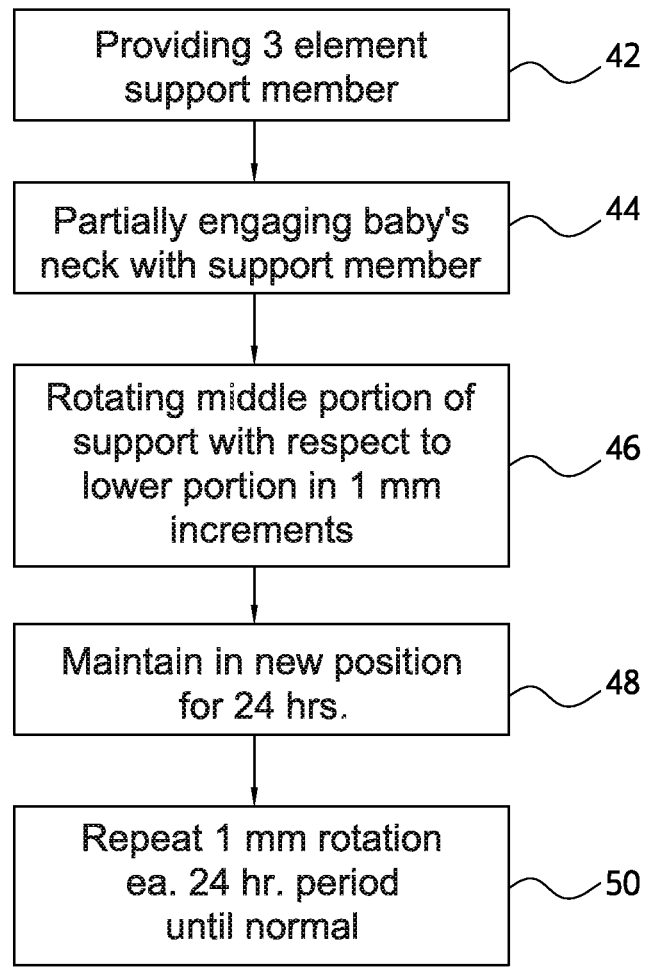
FIG. 4 is a schematic illustration of a device in accordance with the invention illustrating the placement of an individual's head and with the lower portion of the device supported on the patient's shoulders.

As shown in FIG. 4 the method for correcting a skeletal abnormality in a newborn baby's neck includes the following steps. In a first step 42, calls for providing a three element support member as defined in the above-identified orthotic device. Then, in a second step a baby's neck which requires an abnormality adjustment is engaged by the three element support member step 44. To be more specific, the baby's neck is wrapped with the support member extending around the sides and back of the baby's neck. The support member is clamped in place with two clamps, one in a lower portion and one in a middle portion of the neck. The baby's neck in this position includes an abnormality and the positioning of the rotation is adjusted by a knob to accommodate that abnormality. Then the middle portion of the support is rotated by approximately one millimeter in step 46 with respect to the lower portion of the support member. This bias very slight movement of the neck is maintained in this position for 24 hours in step 48. Thereafter the one millimeter rotation is repeated each 24 hour period until the baby's head has been rotated with respect to their torso in steps 50. The above procedure should begin preferably within six hours of a baby's birth but at least within ten to twelve hours of birth and continued until a normal position is reached and stabilized for several days.

While the invention has been described in connection with its preferred embodiments, it should be recognized that changes and modifications may be made therein without departing from the scope of the appended claims.

What is claimed is:

1. An orthotic device for correcting a skeletal abnormality in a newborn baby patient's neck, said device comprising: a three level rigid or semi rigid shell like support adapted to partially encircle a newborn patient's neck and support the patient's head with respect to the patient's torso; wherein a first or lower element defines an inverted frustum of a cone adapted to extend around and abut both sides and back of a lower portion of the patient's neck but opened along the front of the patient's neck with a larger opened base of the inverted cone engaging the patient's shoulder area; clamping means for fastening an upper portion of the first element in spaced relation against the patient's neck without obstructing the patient's esophagus or airway; a second element of said device defines a frustum of a cone adapted to be opened along the front of the patient's neck with its opened smaller lower end engaging a smaller upper end of the first element and rotationally attached thereto; still further the device includes a second clamping element for fastening the second element against the patient's neck without obstructing the patient's esophagus or windpipe; in addition an adjustable mechanism for adjusting the rotational movement between the first element of the device and the second element of the device in one millimeter increments is provided; and finally a third element of the device also defines a frustum of a cone adapted to partially encircle a patient's neck with a smaller end of the frustum of the cone engaging and fixed to an upper larger opening of the second element but flared outwardly at a greater angle than the second element and adapted for supporting a lower portion of the patient's head; wherein said lower element flares outwardly from the upper end of the lower element thereof and said second element flares outwardly from the lower end thereof to the upper larger opening thereof and wherein the upper end of said lower element and the lower end of said second element have equal diameters.

2. An orthotic device for correcting a skeletal abnormality in a newborn baby patient's neck according to claim 1, in which said third element flares outwardly from a vertical axis at an angle of about 45°.

3. An orthotic device for correcting a skeletal abnormality in a newborn baby patient's neck according to claim 2, in which said lower element flares outwardly from the upper end of said element to the larger opened base of said element and said second element flares outwardly from the lower end of said element to the upper larger opening of said element and each of said lower element and said second element flare outwardly at an angle of about 20°.

4. An orthotic device for correcting a skeletal abnormality in a newborn baby patient's neck according to claim 1, in which said three level shell like support is made of a semi rigid plastic.

5. An orthotic device for correcting a skeletal abnormality in a newborn baby patient's neck according to claim 1, in which the three level shell like support is made of a rigid plastic selected from the group consisting of polyethylene, polyvinylchloride, and polyethyleneterephthalate.

6. An orthotic device for correcting a skeletal abnormality in a newborn baby patient's neck according to claim 1, in which said third element flares outwardly from a vertical axis at an angle of between 40° to 50°.

* * * * *